(12) United States Patent
Baumoel et al.

(10) Patent No.: US 6,786,077 B2
(45) Date of Patent: Sep. 7, 2004

(54) WIDE BEAM CLAMP-ON ULTRASONIC DENSITOMETER

(76) Inventors: Joseph Baumoel, 104 Fairway View Dr. The Hamlet, Commack, NY (US) 11725; Douglas Baumoel, 67 Boyles St., Beverly, MA (US) 01915

( * ) Notice: Subject to any disclaimer, the term of this patent is extended or adjusted under 35 U.S.C. 154(b) by 0 days.

(21) Appl. No.: 10/356,194

(22) Filed: Jan. 31, 2003

(65) Prior Publication Data

US 2004/0149013 A1 Aug. 5, 2004

(51) Int. Cl.[7] .............................................. G01N 9/24
(52) U.S. Cl. ........................................................ 73/32 A
(58) Field of Search .............................. 73/32 A, 1.83, 73/24.05, 861.01, 861.02

(56) References Cited

U.S. PATENT DOCUMENTS 3,911,726 A * 10/1975 Georgiev ..................... 73/32 A
5,271,267 A * 12/1993 Baumoel .................... 73/54.41
6,405,603 B1 * 6/2002 Baumoel .................... 73/861.24

* cited by examiner

Primary Examiner—Hezron Williams
Assistant Examiner—John C Hanley
(74) Attorney, Agent, or Firm—F. Chau & Associates, LLC

(57) ABSTRACT

A method for determining the density of a fluid in a pipe. The method includes determining a first, second, and third reference reading of a pipe using a transmitter transducer, a receiver transducer, and a primary receiver transducer. The first reference reading is determined when the pipe is empty. The second reference reading is determined when the pipe contains a reference liquid of known sonic impedance. The third reference reading is determined when the pipe contains an unknown liquid. The liquid sonic propagation velocity of the unknown liquid is measured. The relationship of an impedance of the unknown liquid in relation to the impedance of the reference liquid is determined. Finally, the density of the unknown liquid is determined using the determined relationship of the unknown impedance to the known impedance of the reference liquid divided by the measured liquid sonic propagation velocity of the unknown liquid.

13 Claims, 4 Drawing Sheets

WIDE BEAM CLAMP-ON ULTRASONIC DENSITOMETER

BACKGROUND

1. Technical Field

This disclosure relates to an ultrasonic flowmeter, more particularly, a method and system for determining the density of a fluid flowing through a pipe within a pipe system.

2. Discussion of Related Art

The use of a non-intrusive Clamp-On Wide Beam ultrasonic flowmeter to measure both flow rate and liquid sonic propagation velocity of a liquid in a pipe is known.

A major attribute of the Wide Beam method is that the signal arrives at a point down the pipe wall essentially undistorted, with its amplitude reduced primarily by the extraction of the energy that has been injected into the liquid. There is no amplitude distortion due to internal pipe wall reflections. Accordingly, the measure of the amplitude of the received energy is a function of the energy delivered into the pipe wall.

The energy received by a transducer is dependent on the natural losses in the pipe wall. The natural losses are associated with the material between the transducers and as energy radiates in different paths than that which leads to the transducer. However, the additional loss due to the energy delivered into a liquid or other material inside the pipe will add to this loss. In addition, the received signal amplitude can be affected by other factors, such as a change in gain of an amplifier used to measure the received signal.

Therefore, a need exists to determine additional energy losses of the sonic energy waves, other than due to the presence of liquid, to establish a baseline against which to determine and accurately measure the density of a liquid flowing through a pipe.

SUMMARY OF THE INVENTION

According to an embodiment of the present invention, a system and method is provided which uses a non-intrusive Clamp-On Wide Beam ultrasonic signal to measure liquid density. As will be shown, the density of a liquid flowing through a pipe can be determined as a function of the measured sonic impedance of the container or pipe wall relative to the measured sonic impedance of the liquid divided by the measured liquid sonic propagation velocity of the fluid flowing through the pipe. In addition, a non-intrusive flowmeter can be used to measure the density of a fluid flowing through a pipe by extracting only those functions needed for measuring density, according to another embodiment of the present invention.

In reference to the problem of the received amplitude being affected by other factors, e.g. a change in gain of amplifier used to measure the received signal, the factors can be normalized by measuring the amplitude injected by a transmitter transducer as a reference. Thus, incorporating a reference receiver transducer in the transmitter transducer to determine the strength of transmission can do. An alternative method is to install a separate reference receiver transducer along the pipe wall disposed immediately adjacent to the transmitter transducer and a second receiver transducer, according to another embodiment of the present invention. By measuring the amplitude injected by a transmitter transducer as a reference factor, this will also incorporate any systematic change in the transducer to pipe wall sonic coupling.

Another embodiment of the present invention relates to a method for measuring the density of a fluid in a pipe. The method comprises the steps of determining a first, a second, and a third reference reading of a pipe using a transmitter transducer, a receiver transducer, and a primary receiver transducer coupled to a pipe, wherein the first reference reading is determined when the pipe is empty, the second reference reading is determined when the pipe contains a reference liquid of known sonic impedance within, and the third reference reading is determined when the pipe contains an unknown liquid within. Next, a liquid sonic propagation velocity of the unknown liquid is measured. The relationship between the impedance of the unknown liquid relative to the impedance of the reference liquid is determined. The density of the unknown liquid is measured by using the determined relationship of the unknown impedance to the known impedance of the reference liquid divided by the measured liquid sonic propagation velocity of the unknown liquid.

Further, another embodiment of the present invention relates to a system for measuring density of an unknown liquid having an unknown impedance flowing through a pipe. The system includes an ultrasonic transducer system coupled a pipe segment having a first end and a second end, the ultrasonic transducer system including a transmitter transducer disposed at the first end the pipe segment which generates and transmits sonic energy waves at a known desired rate, a reference receiver transducer disposed immediately adjacent to the transmitter transducer for receiving the sonic energy waves, and a primary receiver transducer disposed at the second end of the pipe segment for receiving the sonic energy waves. The system also includes a sensor for measuring an amplitude of the sonic energy waves at the reference receiver transducer and the primary receiver transducer of a plurality of reference fluids in a pipe system. And, a processor for recording the measured amplitude of the sonic energy waves at the reference receiver transducer and the primary receiver transducer to determine the ratio of the amplitude of the sonic energy waves received at the primary receiver transducer to the amplitude of the sonic energy waves received at the reference transducer and records the liquid sonic propagation velocity of a liquid and uses the ratios and liquid sonic velocity to determine density.

These and other objects, features and advantages of the present invention will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF PREFERRED EMBODIMENTS

The present invention will now be described more fully with reference to the accompanying drawings, in which referred embodiments of the invention are shown. This invention may, however, be embodied in many different forms and should not be construed as being limited to the embodiments set forth herein. Rather, these embodiments are provided so that this disclosure will be thorough and complete, and will fully convey the concept of the invention to those skilled in the art.

The present invention includes a system and method for determining the density of an unknown liquid within a pipe system, which uses a non-intrusive Clamp-On Wide Beam ultrasonic signal used to measure the density of a liquid within a pipe.

Figure 1:
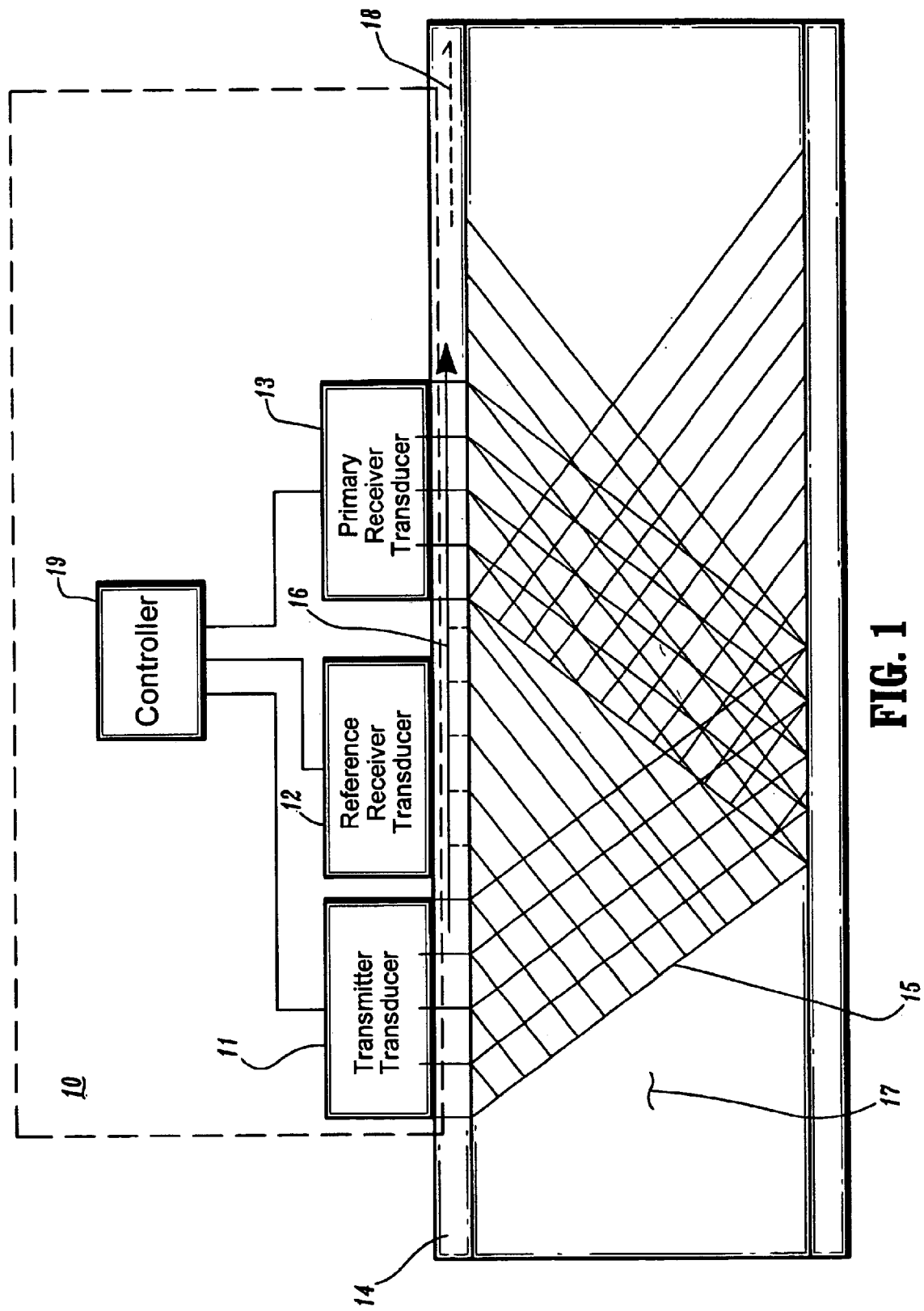
FIG. 1 is a schematic diagram of a pipe system having a flowmeter installed in accordance with an embodiment of the present invention.

FIG. 1 is a schematic diagram illustrating a flowmeter clamped to the outside of a pipe within a pipe system, according to an embodiment of the present invention. More specifically, FIG. 1 illustrates a flowmeter 10 having a controller 19 coupled to a transmitter transducer 11, a reference receiver transducer 12, and a primary receiver transducer 13. In addition, the controller 19 is used for controlling the transmission and reception of ultrasonic signals, and the controller 19 may include a processor (not shown) and a memory (not shown). Alternatively, the controller 19 can send the transducers' 11, 12, and 13 signals to a computer or PC having a stored program, which when executed computes the effects of the parameter measurements, to be described below.

Figure 2:
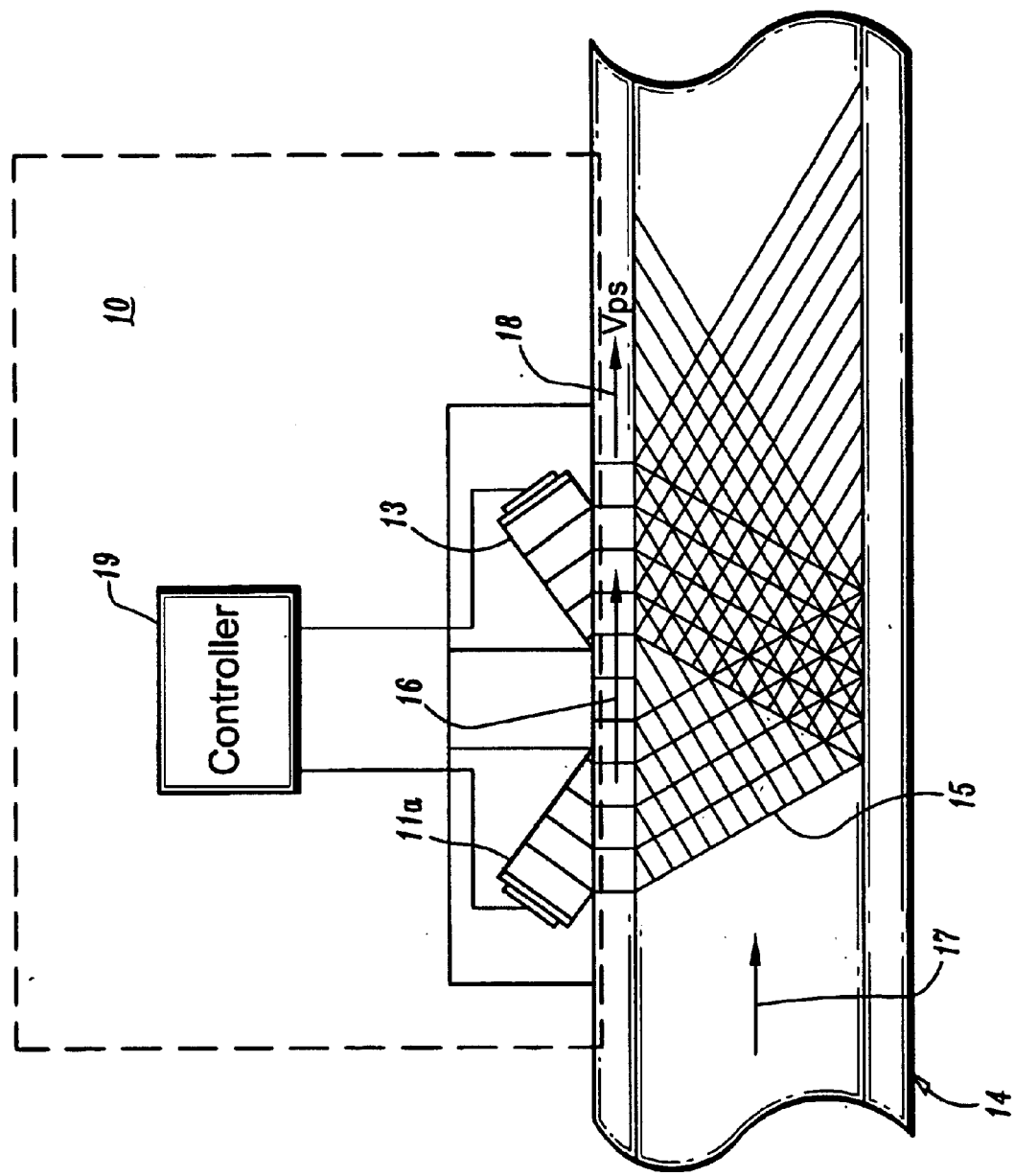
FIG. 2 is a schematic diagram of a pipe system having a flowmeter installed in accordance with another embodiment of the present invention.

FIG. 1 also illustrates the transmitter transducer 11 coupled to a pipe 14 for generating and transmitting sonic energy waves or signals 15 through the pipe wall. After the transmitter transducer 11, a reference receiver 12 is coupled to the outer wall of the pipe 14. After the placement of the reference transducer 12, a primary transducer 13 is coupled to the pipe. In addition, it should also be noted that the reference transducer 12 may be part of the transmitter transducer 11 as shown in FIG. 2, according to another embodiment of the present invention.

A densitometer 10 comprises a controller 19 having a processor and memory, a transmitter transducer 11 coupled to the controller 19, a reference receiver transducer 12 disposed adjacent to the transmitter transducer 11 and coupled to the controller 19, and a primary receiver transducer 13 disposed at a predetermined distance from the reference receiver transducer 12 and coupled to the controller 19, according to another embodiment of the present invention. The densitometer 10 may also be connected to a processor, not shown.

The transmitter transducer 11 transmits a sonic energy wave or signal 15 through the pipe wall, which generates a pipe wall signal 16, and the signal 16 is detected by the reference receiver transducer 12. Thereafter, the signal enters the liquid flow 17 and reflects off the pipe wall to the primary transducer 13, as shown in FIG. 1. The transducers 12 and 13 detect the signal and convey the signal to a processor to determine the amplitude of the signal. The controller 19 having a stored program receives the pipe wall signals from the transducers 12 and 13 and computes the amplitudes of the received signals. The signal received at transducer 12 is used to serve as a reference signal at a known position. The signal received at transducer 13 represents the signal as a function of the energy delivered into the pipe wall and liquid.

The amplitudes at transducers 12 and 13 are measured when the pipe is void of any liquid, an empty pipe, and when a liquid is introduced into the pipe. The amplitudes measured when the pipe is void of any liquid are used to determine the natural losses associated with the pipe, e.g. the losses in the pipe wall as energy radiates in different paths than that which leads to the transducer 13 and losses due to the materials between the transducers 12 and 13. The amplitudes at transducer 12 and 13 measured when liquid is introduced into the pipe are used to determine the energy present between transducers 12 and 13. The introduction of the liquid into the pipe will reduce the amplitude of the signal between transducers 12 and 13. This reduction in amplitude is a function of the transfer of energy extracted by the liquid which is a function of their relative sonic impedances.

A major attribute of the Wide Beam flowmeter is that the signal that arrives at a point down the pipe wall is essentially undistorted, with its amplitude reduced primarily by the extraction of the energy that has been injected into the liquid. Essentially, no amplitude distortion is suffered due to internal pipe wall reflections. Accordingly, the measure of the amplitude of the received energy at transducer 13 is a function of the energy extracted by the liquid and delivered into the pipe wall.

As a Wide Beam sonic wave, as defined previously, travels down a pipe or container wall, hereafter collectively referred to as the pipe wall, it loses energy to any medium in sonic contact with the inner wall of the pipe. The amount of energy that is transmitted into the liquid, and thus removed from the pipe wall, is dependent on the relative sonic impedance of the pipe wall and the liquid, as defined by the following equation:

$$\text{Transmitted wave} = T = 2Zl \ (Zp+Zl)$$

$$\text{Reflected wave} = R = (Zp-Zl)/(Zp+Zl)$$

Where: $Zp$=Pipe wall acoustic impedance
$Zl$=Liquid acoustic impedance

The amplitude received by the primary, or first, receiver transducer is dependent on the natural losses in the pipe wall. The natural losses are in the material between the primary receiver transducer and the transmitter transducer and as energy radiates in different paths than that which leads to the second transducer and also losses in the material between transducers. However, the additional loss due to the energy delivered into a liquid or other material inside the pipe will add to this loss. A measurement of natural energy losses, other than due to the presence of liquid, can establish a baseline against which to determine and accurately measure the liquid losses.

However, the received signal amplitude can be affected by other factors, e.g. a change in gain of an amplifier used to measure the received signal. Therefore to normalize this factor it is desired to measure the energy injected by the Transmit transducer as a reference. Incorporating a reference, or second, receiver transducer in the transmitter transducer to determine the strength of transmission can do this. An alternative method is to install a reference, or second, receiver transducer on the pipe wall just past the location of the transmitter transducer. This will also incorporate, as a reference factor, any systematic change in the transducer to pipe wall sonic coupling. A method for determining the reference reading, or baseline of a pipe and determining the density of an unknown liquid in the pipe is described below.

FIG. 2 is a schematic diagram illustrating a flowmeter 10 clamped to the outside of a pipe within a pipe system according to another embodiment of the present invention. FIG. 2 illustrates a flowmeter 10 having a controller 19 coupled to a transceiver transducer 11A having both a transmitter and a receiver, the transmitter and receiver portion of transducer 11A functions the same as described for the transmitter transducer 11 and reference receiver transducer 12 of FIG. 1. In addition, the controller 19 is used for controlling the transmission and reception of ultrasonic signals. The controller 19 preferably includes a processor (not shown) and a memory (not shown). Alternatively, the controller 19 can send the signals of the transducers 11a and 13 to a computer or PC having a stored program, which when executed computes the effects of the parameter measurements, to be described below.

Figure 3:
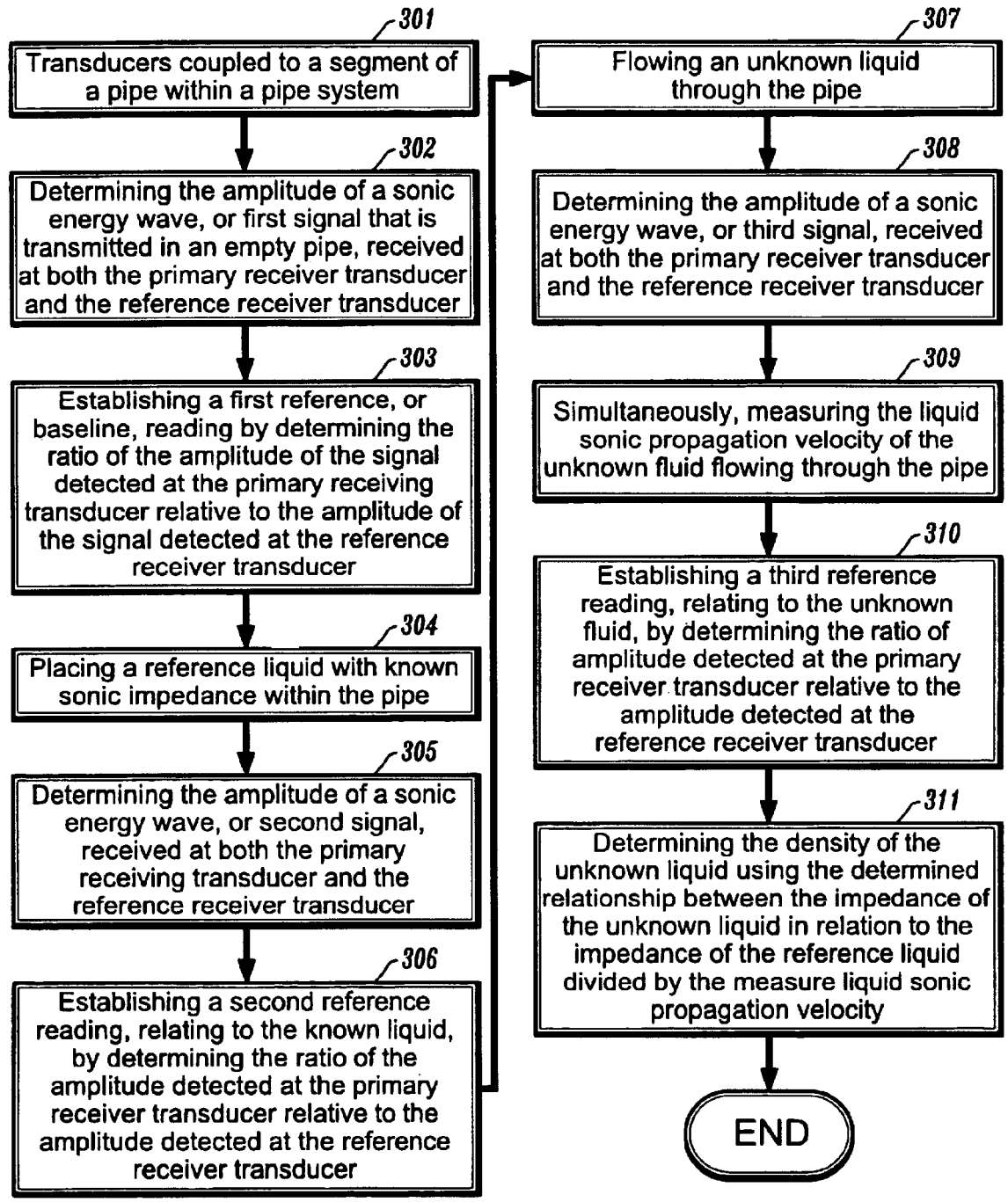
FIG. 3 is a flow diagram for a method for determining the density of an unknown fluid within a pipe system in accordance with an embodiment of the present invention.

FIG. 3 is a flowchart of a method for determining the density of an unknown liquid within a pipe system, according to an embodiment of the present invention. Referring to FIG. 3, initially, the transmitter transducer, reference transducer, and primary transducer are coupled to a segment of a pipe within a pipe system (Step 301). Next, a sonic energy wave(s), or first signal, is transmitted into the pipe, and the amplitude of the first signal received at the reference transducer and the primary transducer is then determined (Step 302). Next, a first reference reading, or baseline, is established by determining the ratio of the amplitude of the first signal detected at the primary receiving transducer relative to the amplitude of the first signal detected at the reference receiving transducer (Step 303). This reference reading incorporates all energy losses associated with an empty pipe.

Next, a reference liquid, e.g. water, with known sonic impedance is feed into the pipe (Step 304). Then, a second sonic energy wave, or second signal, is transmitted into the pipe through the pipe wall, and the amplitude of the second signal at both the primary and reference transducer is determined (Step 305). A second reference reading is established by determining the ratio of the amplitude of the second signal detected at the primary receiving transducer relative to the amplitude of the second signal detected at the reference receiving transducer for the reference liquid (Step 306). This establishes the following reference factor:

$$Rtw = Kw$$

Where Rtw=Ratio of Receive Transducer Amplitudes with Water in Pipe
Kw must be less than Ke, where Ke is the Ratio constant when the pipe is empty.

Next, An unknown liquid is feed into the pipe system (Step 307). A third sonic energy wave, or third signal, is transmitted through the pipe wall and into the unknown liquid, and the amplitude of the third signal at both the primary and reference transducer is determined (Step 308). And, simultaneously, the liquid sonic propagation velocity of the unknown liquid is measured (Step 309). A third reference reading K?, which is the ratio constant when the pipe has an unknown liquid therein, is established by determining the ratio of the amplitude of the third signal detected at the primary receiving transducer relative to the amplitude of the third signal detected at the reference receiving transducer for the unknown liquid (Step 310).

Finally, since all factors remain the same except for the substitution of the liquids, it is evident that the relative difference in the three reference readings, or received amplitudes, is due to the relative sonic impedance of the materials contacting the inside of the pipe. The following equations can be used to compute the effect of these sonic impedance and the amplitude of their respective Received Ratio amplitudes:

$$Ke - Kw = f(Zp - Zw)/(Zp + Zw)$$

And:

$$Ke - K? = f(Zp - Z?)/(Zp + Z?)$$

K?, Ke and Kw are measured, and Zp is known, these two equations can be solved for Z? in relation to Zw, which represents liquid acoustic impedance of water.

Figure 4:
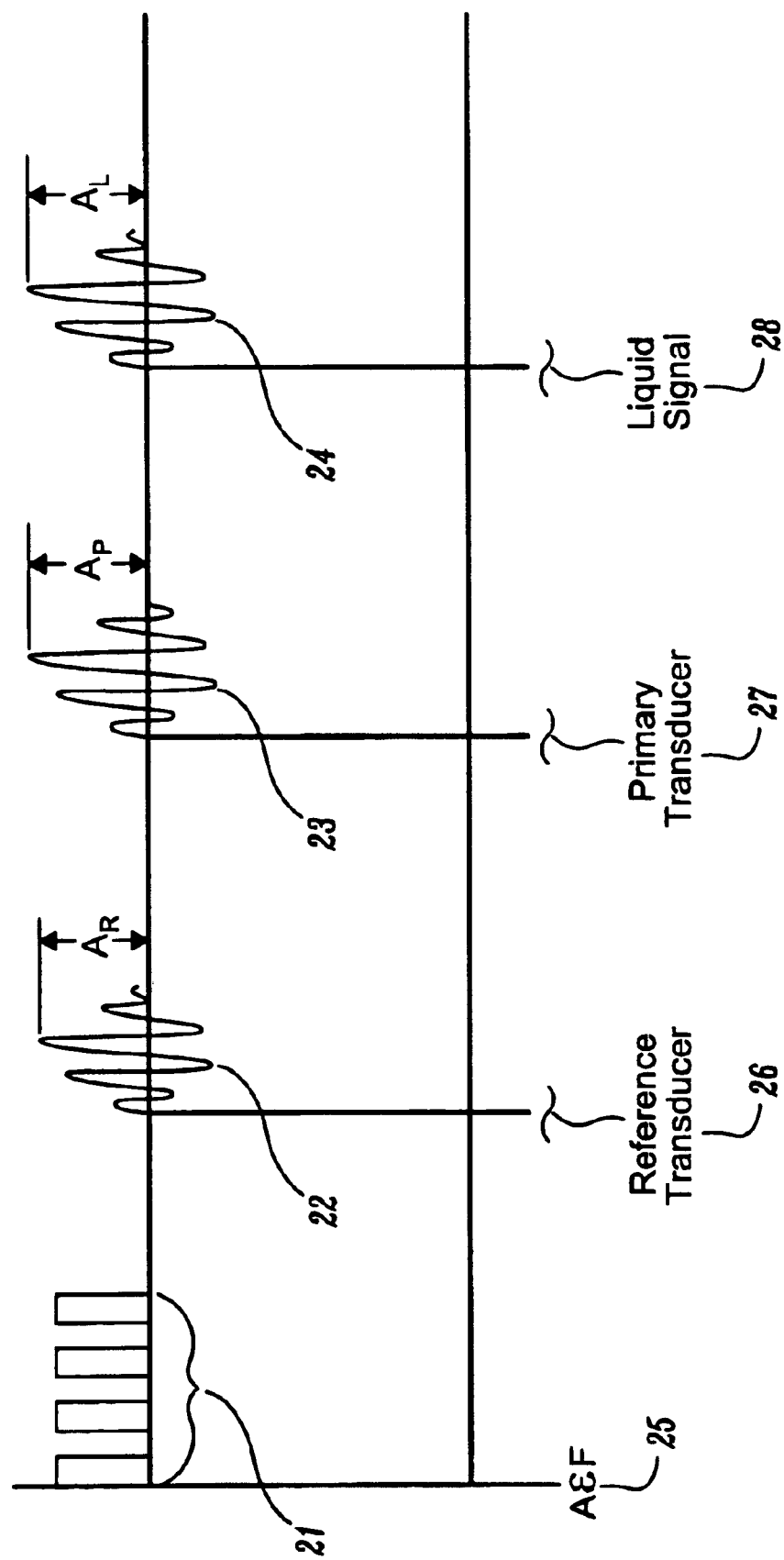
FIG. 4 depicts a time diagram of a sonic energy or signal generated by a transmitter transducer and being detected by a plurality of receiver transducers detecting the signal, according to an embodiment of the present invention.

And, since $Z? = d? Vs$, where D? is the unknown density, Vs is the measured liquid sonic propagation velocity, and the relationship of Z? to Zw has been determined using the equations above, the density of the unknown liquid may be determined using the following equation (Step 311):

FIG. 4 depicts a time diagram of a sonic energy wave or signal generated by a transmitter transducer and the amplitude of the signal received by the receiver transducers, according to an embodiment of the present invention. Referring to FIG. 4, a sonic energy wave or signal 21 is transmitted at time 25 by a transmitter transducer 11. The reference receiver transducer 12 detects the signal 22 transmitted by the transmitter transducer 11 at time 26 ($\tau$ reference tranducer). The signal then travels through the liquid flow 17 reflecting off the pipe wall. And, the primary receiver transducer 13 detects the signal 23 at time 27 ($\tau$ primary transducer).

The signal 24 represents the liquid signal at time 28 ($\tau$ liquid signal), which is the arrival time relative to the start time 25. Thus, the amplitudes of the signals, such as amplitude $A_L$, are used to determine the sonic impedance z?, which is the impedance of an unknown liquid and the time of arrival information is used to determine the sonic velocity of the liquid.

Density is then determined by dividing the determined impedance of the unknown liquid by the measured liquid sonic velocity of the unknown liquid flowing through a pipe system, Having described preferred embodiments for a novel densitometer for pipe systems, which is meant to be illustrative and not limiting, it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A method for measuring the density of a fluid in a pipe, comprising the steps of:

determining a first, a second, and a third reference reading of a pipe using a transmitter transducer, a receiver transducer, and a primary receiver transducer coupled to a pipe, wherein the first reference reading relates to the pipe void of any liquid, the second reference reading relates to the pipe having a reference liquid of known sonic impedance within, and the third reference reading relates to the pipe having an unknown liquid of unknown density and unknown sonic impedance within;

measuring a liquid sonic propagation velocity of the unknown liquid;

determining an impedance of the unknown liquid based upon the known impedance of the reference liquid and the first, second, and third reference readings; and determining the density of the unknown liquid based upon the determined unknown impedance and the measured liquid sonic propagation velocity of the unknown liquid.

2. The method as recited in claim 1, wherein the step of determining a first reference reading of an empty pipe, a pipe void of any liquid, further comprises the steps of:
- transmitting a first signal into an empty pipe;
- determining the amplitude of the first signal detected by a reference receiver transducer;
- determining the amplitude of the first signal detected by a primary receiver; and
- establishing the first reference reading by determining the ratio of the amplitude of the first signal detected at the primary receiver transducer relative to the amplitude of the first signal detected at the reference receiver transducer.

3. The method as recited in claim 2, wherein the first signal is a wide beam ultrasonic signal.

4. The method as recited in claim 1, wherein the step of determining a second reference reading of the pipe having a reference liquid of known sonic impedance further comprises the steps of:
- placing a reference liquid with known sonic impedance within the pipe;
- transmitting a second signal into the pipe having the reference liquid;
- determining the amplitude of the second signal detected by a reference receiver transducer;
- determining the amplitude of the second signal detected at a primary receiver transducer; and
- establishing a second reference reading by determining the ratio of the amplitude of the second signal detected at the primary receiver transducer to the amplitude of the second signal detected by reference receiver transducer.

5. The method as recited in claim 4, wherein the second signal is a wide beam ultrasonic signal.

6. The method as recited in claim 1, wherein the step of determining a third reference reading of the pipe having an unknown liquid of unknown density and unknown sonic impedance further comprises the steps of:
- flowing an unknown liquid with an unknown density and unknown impedance through the pipe;
- transmitting a third sonic energy wave, or a third signal, into the pipe having the unknown liquid;
- determining the amplitude of the third signal detected by a reference receiver transducer;
- determining the amplitude of the third signal detected by a primary receiver transducer; and
- establishing a third reference reading by determining the ratio of the amplitude of the third signal detected at the primary receiver transducer to the amplitude of the third signal detected by reference receiver transducer.

7. The method as recited in claim 6, wherein the third signal is a wide beam ultrasonic signal.

8. The method as recited in claim 1, wherein the step of determining the density of the unknown liquid comprises solving the following equation:

$$d? = Z?/V_s, \text{ where}$$

d?=the density of the unknown liquid;
Z?=the determined impedance of the unknown liquid; and
$V_s$=the liquid sonic propagation velocity of the unknown liquid.

9. The method as recited in claim 1, wherein the unknown liquid is a liquid of known mixture having an unknown density and unknown impedance.

10. A method for determining the density of an unknown liquid in a pipe using an ultrasonic measuring device comprising a transmitter transducer, a reference receiver transducer disposed adjacent to the transmitter transducer, and a primary receiver transducer disposed at a predetermined distance from the reference receiver transducer, wherein the method comprises the steps of:
- transmitting a sonic energy wave, or signal, by the transmitter transducer through a pipe wall at a known rate without any liquid in the pipe, wherein the signal travels from the transmitter transducer to the reference transducer and then the signal reflects off the pipe wall to the primary receiver transducer;
- determining the ratio of amplitude of the signal detected by the primary receiver transducer relative to the amplitude of the signal detected by the reference receiver transducer;
- feeding a reference liquid with known sonic impedance into the pipe system;
- transmitting a second signal;
- determining the ratio of the amplitude of the second signal detected by the primary receiver transducer relative to the second signal detected by the reference receiver transducer;
- flowing through the pipe an unknown liquid;
- transmitting a third signal;
- determining the ratio of the amplitude of the third signal detected by the primary receiver transducer relative to the amplitude of the third signal detected by the reference receiver transducer;
- measuring the liquid sonic propagation velocity of the unknown liquid flowing through the pipe;
- determining the impedance of the unknown liquid the based upon the impedance of the reference liquid and the determined ratios; and
- determining the density of the unknown liquid based upon the determined impedance of the unknown liquid and the measured liquid sonic propagation velocity of the unknown liquid flowing through the pipe.

11. A system for measuring density of a liquid, comprising:
- an ultrasonic transducer system coupled to a pipe, the ultrasonic transducer system including a transmitter transducer coupled to the pipe which generates and transmits sonic energy waves at a known desired rate, a reference receiver transducer coupled to the pipe and disposed adjacent to the transmitter transducer for receiving the sonic energy waves, and a primary receiver transducer coupled to the pipe and disposed at a predetermined distance from the transmitter transducer for receiving the sonic energy waves;
- a sensor for measuring an amplitude of the sonic energy waves at the reference receiver transducer and the primary receiver transducer; and
- a processor means for recording the measured amplitude of the sonic energy waves at the reference receiver transducer and the primary receiver transducer and determining the ratio of the amplitude of the sonic energy waves received at the primary receiver transducer to the amplitude of the sonic energy waves received at the reference transducer for an empty pipe and for each of a plurality of fluids successfully fed into the pipe, one being an unknown liquid having an unknown density and sonic impedance, and for computing and recording the liquid sonic propagation velocity of the unknown liquid, and using the determined ratios and the liquid sonic propagation velocity of the unknown liquid to determine the density of the unknown liquid.

12. The system as recited in claim 11, wherein the plurality of fluids successively fed into the pipe are a reference liquid having a known sonic impedance, and the unknown liquid of unknown density and unknown sonic impedance.

13. The system as recited in claim 12, wherein determining density of the unknown liquid using the ratios and liquid sonic velocity comprises solving the formula:

$$d = Z/V_s, \text{ where}$$

*d=the density of the unknown liquid;*

Z=the determined impedance of the unknown liquid; and $V_s$=the liquid sonic propagation velocity of the unknown liquid.

* * * * *